United States Patent [19]

Cranmer

[11] 4,037,200
[45] July 19, 1977

[54] BRAILLE DISPLAY SWITCHING MATRIX AND CIRCUIT UTILIZING THE SAME

[76] Inventor: Terrence V. Cranmer, 523 Pawnee Trail, Frankfort, Ky. 40601

[21] Appl. No.: 626,257

[22] Filed: Oct. 28, 1975

Related U.S. Application Data

[63] Continuation-in-part of Ser. No. 515,363, Oct. 16, 1974.

[51] Int. Cl.² .............................................. H04Q 5/14
[52] U.S. Cl. ........................... 340/166 R; 340/365 S; 340/365 R; 340/365 C; 340/384 E; 340/336
[58] Field of Search .............. 340/166 R, 365 C, 345, 340/365 S, 365 R; 179/90 K, 2 R; 317/DIG. 2; 35/35 A

[56] References Cited

U.S. PATENT DOCUMENTS

| | | | |
|---|---|---|---|
| 3,488,449 | 1/1970 | Scheitler | 179/90 K |
| 3,523,161 | 8/1970 | Lewin | 179/2 R |
| 3,576,433 | 4/1971 | Lee | 235/153 |
| 3,584,398 | 6/1971 | Meyer | 328/59 |
| 3,629,665 | 12/1971 | Hoste | 317/DIG. 2 |
| 3,725,906 | 4/1973 | Quick | 340/365 S |
| 3,766,404 | 10/1973 | Larson | 317/DIG. 2 |
| 3,845,473 | 10/1974 | Kawashima | 340/365 S |
| 3,877,029 | 4/1975 | Larson | 340/365 R |

*Primary Examiner*—Harold I. Pitts
*Attorney, Agent, or Firm*—Donald L. Cox

[57] ABSTRACT

A switching matrix adapted to interface blind persons with electronic signals of the type used to drive a visual digital display device is disclosed. The matrix includes at least one series of raised electrically conductive terminals grouped into sets of braille coded characters representative of the digits 0 through 9 mounted on, but insulated from, an electrically conductive substrate. Each set is adapted to short circuit to the surrounding substrate when touched with a fingertip, thus forming a touch controllable switch.

An electronic circuit employing the matrix is also disclosed which produces an audible signal when the user touches a set of the terminals energized by a signal driving the corresponding digit of a visual digital display device.

2 Claims, 8 Drawing Figures

BRAILLE DISPLAY SWITCHING MATRIX AND CIRCUIT UTILIZING THE SAME

CROSS-REFERENCE TO RELATED APPLICATION

This application is a continuation-in-part of my previously filed co-pending application entitled Braille Display Switching Matrix, Ser. No. 515,363, filed Oct. 16, 1974.

BACKGROUND OF THE INVENTION

The subject invention relates to a novel finger-operated switching means adapted to interface blind persons with a wide variety of instruments which employ electronically operated visual display devices.

As a result of recent rapid developments in both computer and electronic microcircuit technology there has been a wide proliferation of devices having visual digital output display. Examples of such now well-known devices include digital computers, desk and hand calculators, stop watches, clocks, accounting machines, and the like, to name but a few. Moreover, because it is now readily possible to package the relatively large amount of circuitry needed to convert analog information into digital form for display purposes, a great variety of electronic instruments now employ digital output and display logic. Digital voltmeters, pH meters and other electronic test equipment are typical examples of the foregoing. As a matter of fact, digital display devices are now preferred in the art in most instances over the heretofore widely used analog display devices such as meter movements and the like.

In practice, of course, such visual digital display devices cannot be utilized by blind persons. However, the electronic digital signals developed to drive such display devices, whether alphabetic or numeric in character, readily lend themselves to conversion to corresponding audible signals for interpretation by the blind. By means of my invention, a blind person having a fundamental knowledge and proficiency in the use of braille reading technique can interpret alphabetic or numeric digital signal information of the type employed to drive the aforementioned digital display devices.

SUMMARY OF THE INVENTION

It is an object of the present invention to provide a novel touch controlled switching means adaptable to the interfacing of a blind person with conventional visual digital display circuitry.

It is a further object of the instant invention to provide an electronic circuit utilizing a touch controlled switching matrix to produce an audible tone indicative of the presence of a digit in a visual digital display device.

Briefly, in accordance with the instant invention, there is provided a switching matrix having an electrically conductive substrate. At least one series of electrical terminals, representative of the various informational characters is disposed on the substrate. Means is provided for insulating the terminals from the substrate in such a manner as to permit any selected one of the terminals to be shorted with a finger to the substrate.

Additional objects, features and advantages on the instant invention will become apparent to those skilled in the art from the following detailed description and attached drawings on which, by way of example, only the preferred embodiments of the instant invention is illustrated.

DESCRIPTION OF THE PREFERRED EMBODIMENTS

Figure 1:
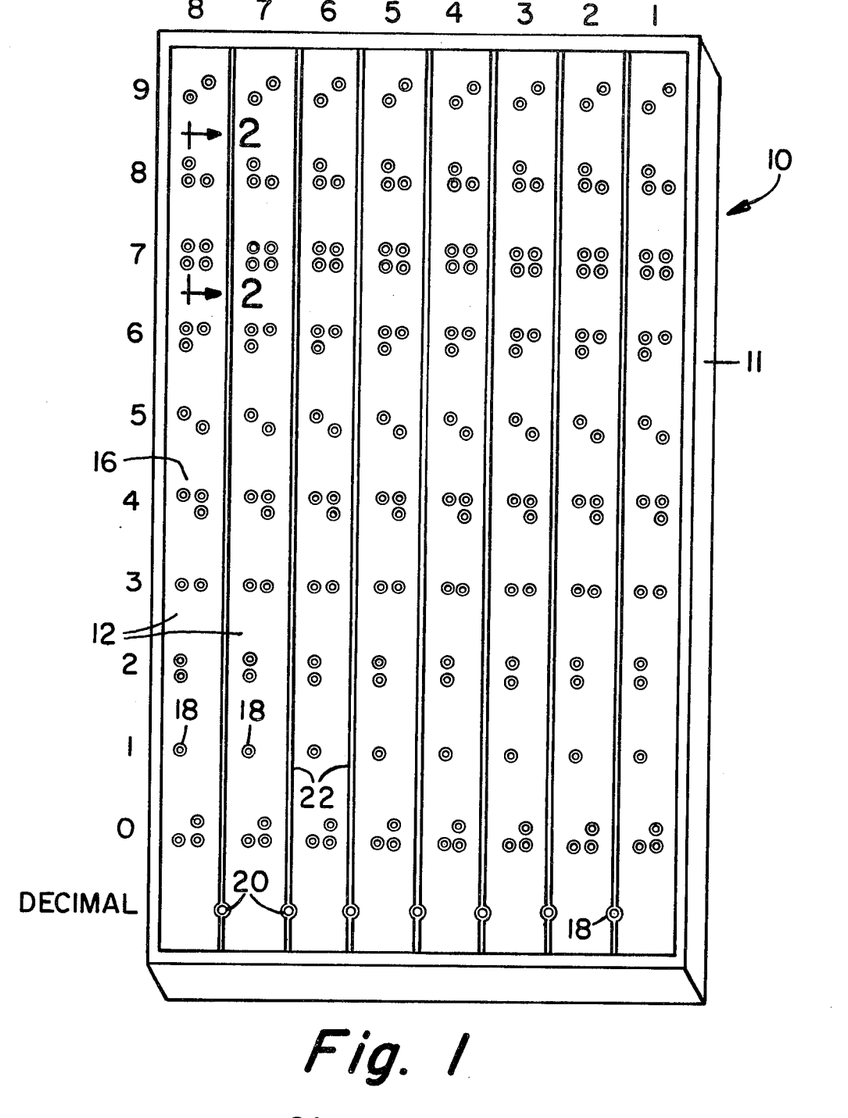
FIG. 1 shows an oblique projection of a touch operated switching matrix, illustrating one embodiment of the instant invention.
Figure 2:
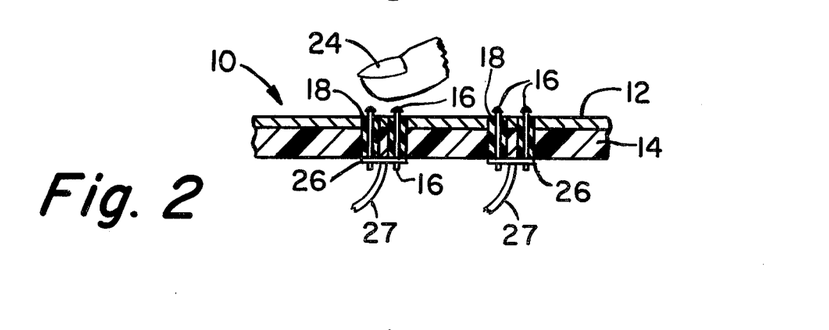
FIG. 2 is a fragmented cross-sectional view of a portion of the switching matrix shown in FIG. 1 as viewed along line 2—2 thereof.

Referring to FIGS. 1 and 2, there is shown, in a preferred embodiment of the instant invention, a switching matrix 10 for use in association with digital circuit logic, now shown. The matrix 10 includes a housing 11, an electrically conductive substrate 12 which may be constructed of copper, aluminum or any other suitable electrically conductive material. The substrate 12 is preferably formed in any well-known manner upon a base 14 of electrically insulative material such as glass, plastic or the like. The housing 11 should also be made of a suitable insulation material so that the substrate 12 will not accidentally short circuit when placed in use on a metal table top.

Upon the substrate 12 there is arranged, in eight separate columns, numbered 1 through 8 in FIG. 1, a plurality of raised and grouped terminals 16, each group in a single column being arranged to form a touch recognizable code representative of a different digit of the decimal system 0 through 9. In the instant example, the terminals 16 are grouped into sets of from one to three members to form the familiar and widely used braille numerical code. Any other type of coding could, of course, be employed to represent the decimal digits contained in each column. The decimal digit represented by each braille coded grouping of the terminals 16 in each of the eight columns is indicated along the left hand side of the matrix 10 of FIG. 1. Instead of numerical characters, the terminals 16 could be grouped to form braille coded alphabetical characters in the same manner, whereby the description of braille coded decimal characters is exemplary only.

Each of the terminals 16 must be electrically insulated from the substrate 12. This may be accomplished either by countersinking a circular portion of the substrate 12 around the terminals 16 in the usual manner or by employing feedthrough insulators 18 as shown most clearly in FIG. 2.

Where more than one column or series of grouped terminals 16 are employed to represent numbers having more than a single digit, as in the instant example, the substrate 12 may be electrically divided into isolated segments or portions. Each such segment or portion of the substrate 12 contains a single column of the terminals 16 representing the digits 0 through 9. The substrate 12 may thus be divided by providing channels or gaps 22 therein extending the entire length of the substrate 12 between adjacent columns of the braille coded groups of the terminals 16. Division of the substrate 12 into such electrically isolated columnar segments is only necessary where the matrix is to be used in conjunction with multiplexed display devices.

Along the bottom row of the matrix 10, opposite the term DECIMAL in FIG. 1, there are a series of terminals 20 representative of a decimal point character. The decimal terminals 20 may be positioned within the gaps 22 between adjacent columnar portions of the substrate 12 indicative of a decimal point position between two adjacent digits of a number. In so positioning the decimal terminals 20, it may be necessary to countersink a circular portion through the substrate 12 around the terminals 20 to insure that the terminals 20 will be fully insulated from surrounding portions of the substrate 12 in the same manner as was previously explained with reference to insulation of the coded terminals 16. In the alternative, rather than countersinking the substrate 12, feedthrough insulators may be used around the terminals 20 in the same manner as illustrated with respect to the insulators 18 used around the terminals 16.

Referring specifically to FIG. 2, the braille code groupings of the terminals 16 should be closely spaced so as to permit each such group to be fully contacted with a fingertip 24. Furthermore, each adjacent grouping of the terminals 16 representative of different digits should be spaced apart a sufficient distance to allow fingertip recognition of each different digit. Thus the fingertip 24 should not overlap so as to touch two adjacent groups of the terminals 16 at the same time.

The terminals 16 and 20 feed through the substrate 12 and base 14 into the interior or the housing 11. Each of the terminals 16 and 20 of a given braille coded group are electrically connected together in any convenient manner such as by means of a jumper 26. A signal may be fed to each braille coded group of the terminals 16 and 20 from an external digital date source by means of wires 27. It should also be noted that the same type of switching matrix can be arranged for the interpretation of alphabetical information or a combination of alphabetical and numerical information simply by establishing grouped series of terminals 16 in columnar form arranged in an alphabetic or alphanumerical code. In the case of alphabetic arrangement there would be a total of 26 grouped terminals in a column representing each letter of the alphabet.

Figure 3:
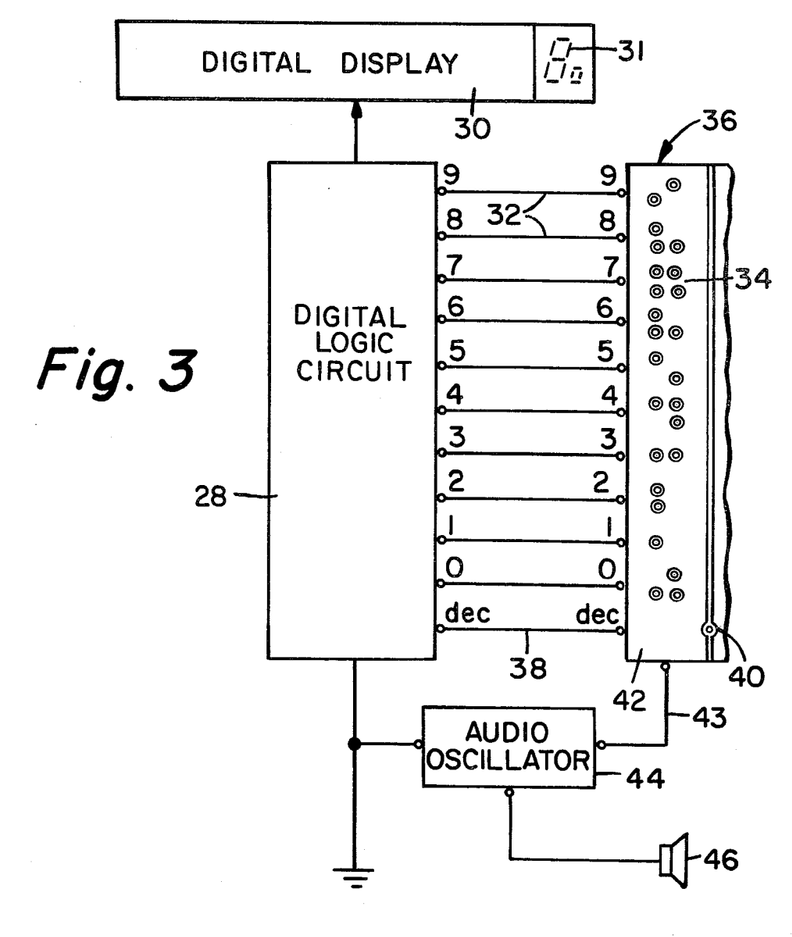
FIG. 3 shows a functional block diagram illustrating the use of the switching matrix of the instant invention in association with digital display logic and audio circuitry, thus illustrating another preferred embodiment of the instant invention.

Referring now to FIG. 3, there is shown a digital logic circuit 28 which may be any well-known prior art device employing electronic digital logic such as a desk or hand calculator, accounting machine, stop watch, clock, voltmeter or the like. The output signal from the circuit 28 drives any well-known type of visual digital display device 30 such as one employing light emitting diodes 31, for example. The device 30 may have any desired number of digits of display capability. Typically, electronic pocket calculators have 8 digit display capability while other machines may use 10 or 12 digit display devices. In any case, the instant example will treat only the logic necessary to utilize the instant invention with a single digit of display capability since additional display capability would be handled in the same way.

Ten decimal output signal lines 32 from the logic circuit 28 are connected as previously explained with reference to FIG. 2 to corresponding coded groups of terminals 34 on a switching matrix 36. Thus, for a given single digit of decimal information to be visually displayed on the display device 30, 10 lines 32 capable of furnishing digital signals to a single column of the matrix 36 are connected to the corresponding code group of the terminals 34. An eleventh output line 38 carries decimal information from the circuit 28 to a decimal terminal 40 of the matrix 36 when more than one column of numerical information is to be read.

The matrix 36 thus functions as a finger-activated switch with an electrically conductive substrate 42 being connected by a line 43 to the signal input terminal of an audio oscillator 44. The oscillator 44, in turn, drives a speaker 46 to generate an audible tone whenever the input line 43 introduces a signal thereto. Such a signal will occur on the line 43 whenever the finger of a person touches one of the braille coded terminal groups 34 to which a signal is applied along one of the lines 32, while at the same time shorting the active terminal group 34 to the substrate 42 through the resistance of the fingertip.

A blind person can, therefore, interpret by touch the particular braille coded terminal group 34 which produces an audible tone upon touching such terminal group, whereby he determines the numerical digit then being visually displayed in the corresponding column of the visual display device 30. If the terminal 40 also produces an audible tone upon touch, the user also recognizes the position of a decimal point appearing between corresponding columns of digits in the visual display 30.

Figure 4:
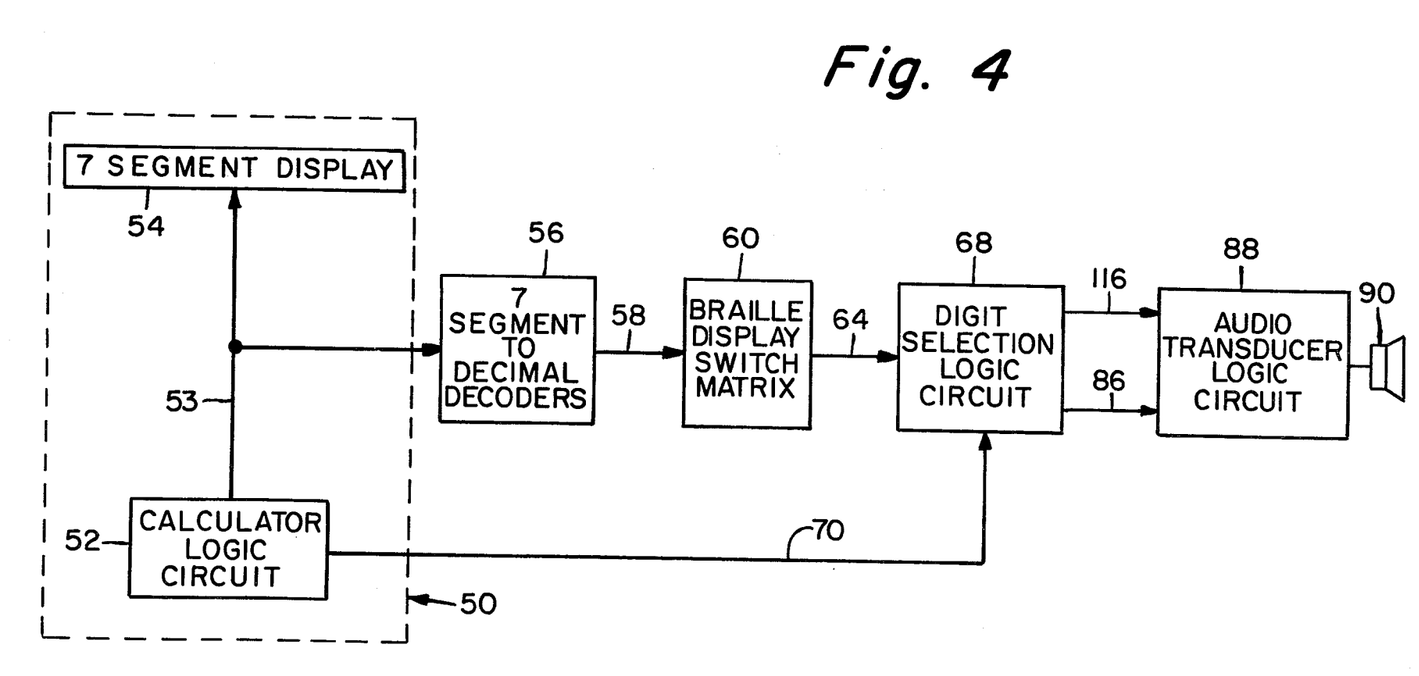
FIG. 4 is a block diagram of the circuit logic employed with the switching matrix of the instant invention to interface a blind person with an electronic instrument having a visual digital display device, thus illustrating another preferred embodiment of the instant invention.

Referring now to FIG. 4, there is shown an electronic hand calculator 50 of the usual and well-known type having a calculator logic circuit 52 adapted to perform various mathematical computations, the output 53 of which is connected to a visual digital register or display 54, an example of which is manufactured by Canon, Inc. A complete schematic diagram of the circuitry and an explanation of the operation thereof will be found in the "Canon Palmtronic LE-80 Service Guide," copyright 1973 by Canon, Inc.

The calculator 50 of the present example employs an 8 digit visual display containing an overflow and minus sign indicator. In each of the digits positions of the 8 digit display 54, there is found a 7-bar light emitting diode (LED) assembly, by means of which all of the digits 0 through 9 can be displayed depending upon the particular combination of bars energized by driving signals from the calculator logic circuit 52. Also included in each digit position of the display 54 is a dot type LED which, when energized by a decimal point signal from the logic circuit 52, indicates the position of a decimal point in the number being displayed, if any. A representation of one such digits position, the units position, of this type of display is seen at the far right of the digital display 30 of FIG. 3 and is commonly referred to as a 7-segment digital display. Thus in order to operate such a 7-segment display, the driving signals for each digits position, as generated by the calculator circuit 52, must be coded in conventional 7-segment logic.

Figure 5:
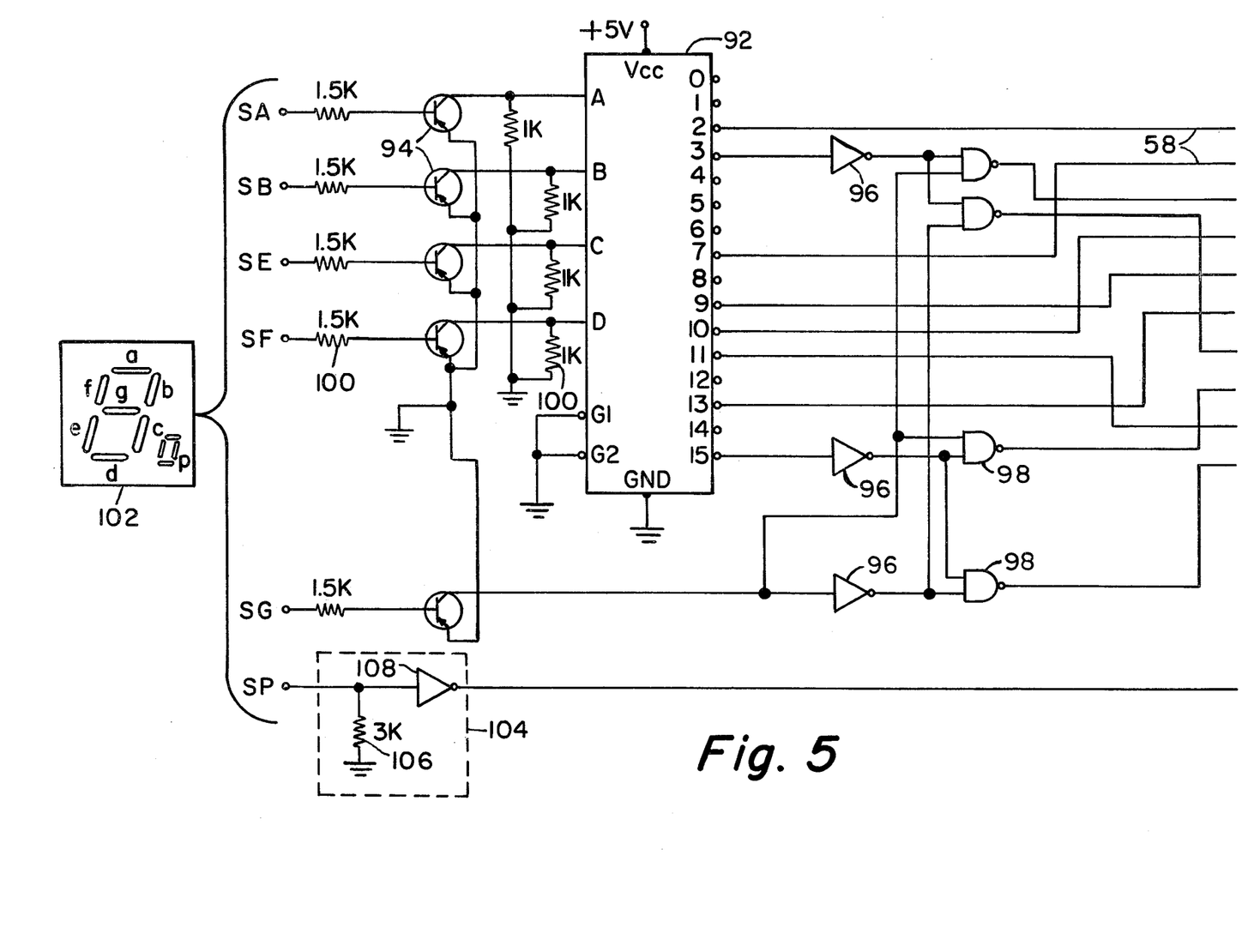
FIGS. 5 and 5a show one example of 7-segment to decimal decoder circuitry which may be used in the circuit logic of FIG. 4.

On the other hand, since the braille display switching matrix of the instant example is constructed to handle only signals coded in decimal logic, it is first necessary to sample the 7-segment signals which drive each column or digit position of the display 54 and convert said signals into a corresponding decimal code. This conversion is accomplished in any well-known manner by means of a 7-segment to decimal decoder 56. One example of a satisfactory decoder circuit for this purpose is shown in FIG. 5 and may be found in an article entitled, "Providing a decimal output for a calculator chip" by Jack Lambert as published in the Aug. 8, 1974, issue of *Electronics* magazine. The decoder circuit 56 as shown in FIG. 5 will be explained in more detail presently, but here, it may simply be noted that the decoder output lines 58, 10 in number, provide decimal coded information to a braille display matrix 60 equivalent to the 7-segment coded information introduced to the decoder 56. The decoder 56 as shown in FIG. 5 will convert a 7-segment input signal as used to drive the digits position of the display 54 into corresponding decimal coded signals, which latter signals are applied through lines 58 to a column of braille grouped terminals 62 on the matrix 60. In the multiplexing system of the instant example, each like number or digit terminal group 16 (FIG. 1) may be electrically connected in common, reading horizontally across the matrix 10.

Figure 5A:
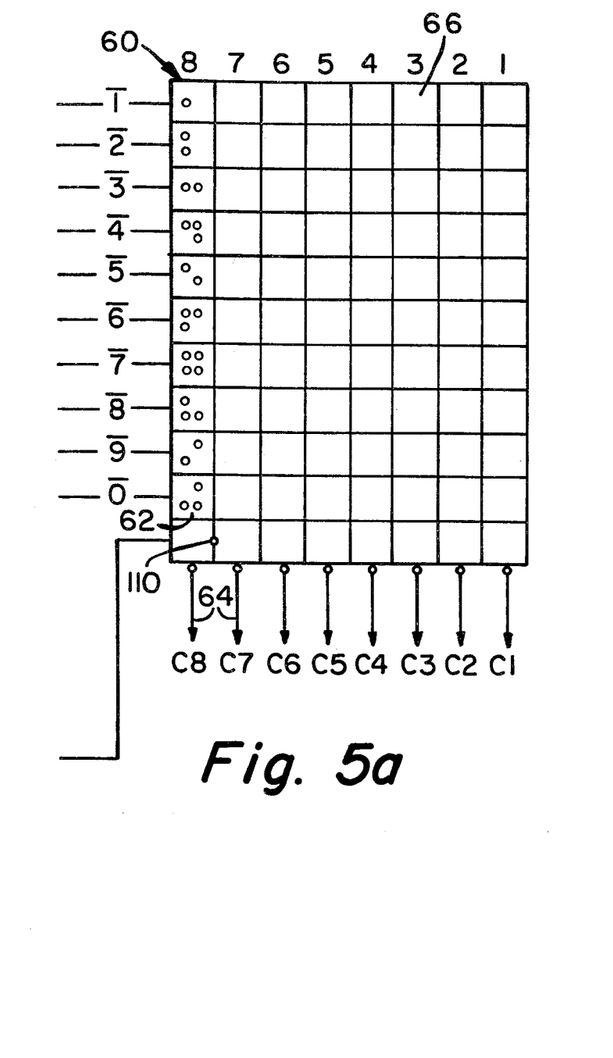

The matrix 60 will have one column of braille coded terminals 62 representative of the digits 0 through 9, for each digits position of the display 54, or a total of 8 such columns in the instant example. A series of 8 matrix output lines 64, designated C1 through C8 in FIG. 5a, are connected to 8 different electrically separate portions of electrically conductive substrate 66 on the matrix 60. Each such portion of the substrate 66 contains a different one of the 8 columns of braille coded terminals 62 thereon.

Figure 6:
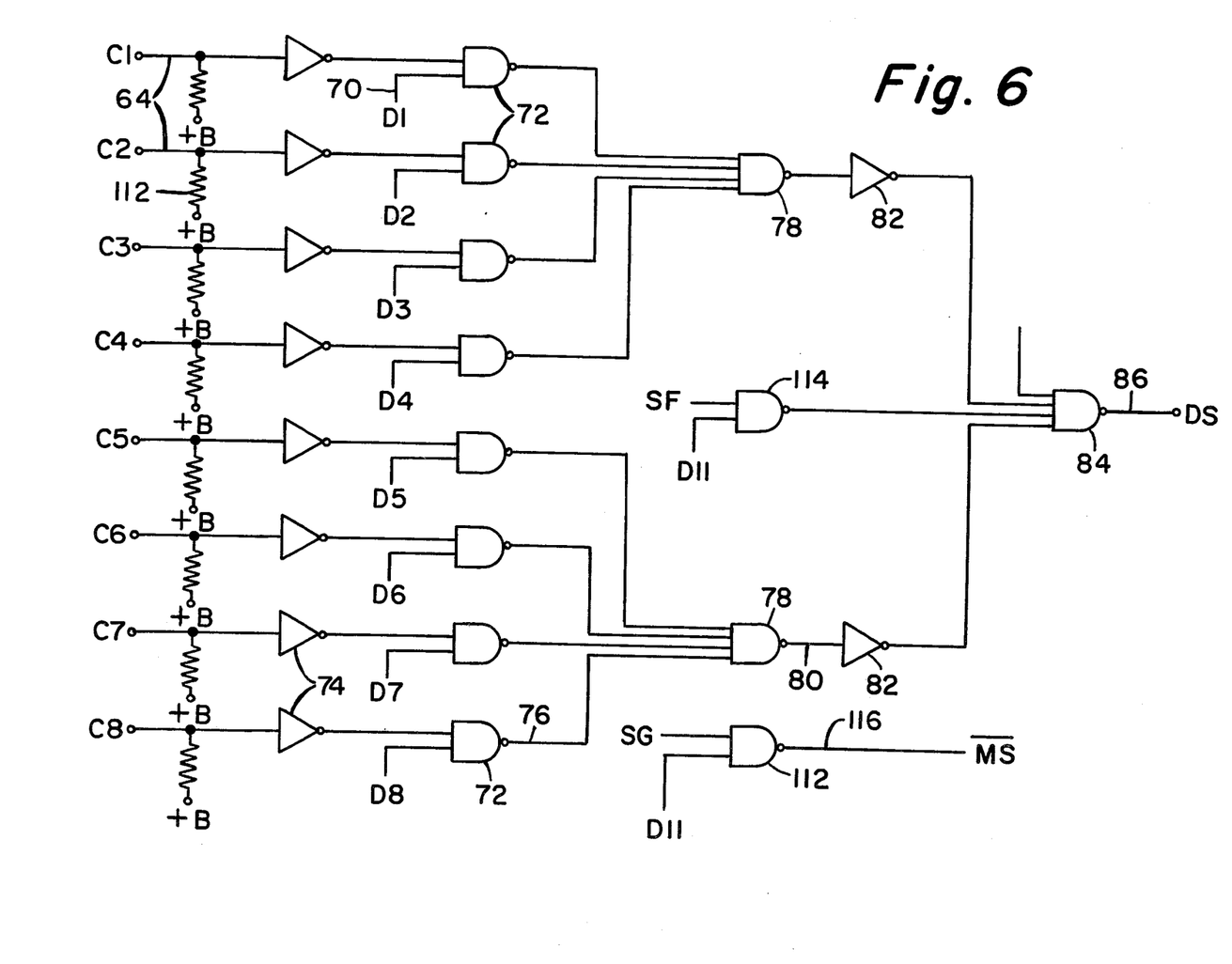
FIG. 6 shows one example of digit selection logic circuitry which may be used in the circuit logic of FIG. 4.

Referring now to FIGS. 4, 5 and 6, the matrix output lines 64 are connected to a digit selection logic circuit 68, one example of which is shown in FIG. 6. Many of the most popular hand calculators in use today, such as the calculator 50 of the present example, employ a system of time division multiplexing wherein the 7-segment driving signals applied to the various digits positions of the display 54 are intermittant or pulsed rather than continuous signals. For example, a set of 7-segment pulses representative of a digit to be displayed in the units position of the display 54 will occur in a very short time span, say 3 microseconds. Over the same time span, a clock or timing pulse, called a D signal will be generated by the calculator logic circuit 52 which will gate the units digits position of the display 54 into an operative state, all in a manner well known in the art. All of the remaining digits positions of the display 54 will remain inoperative during this time period so that the 7-segment digit signals simultaneously occurring will appear only in the units digit position of the display 54.

During the next 3 microsecond period, a second timing pulse will gate the 10's digit position of the display 54, during which period a 7-segment signal will be generated by the circuit 52 representative of the digit to be displayed in that digits position. During this latter period, all of the digits positions of the display 54 are inoperative except the 10's position, in which appears the 10's position digit then being generated by the circuit 52.

The process continues during successive 3 microsecond periods, during which succeeding periods the remaining digits of the display 54 are generated and displayed therein one at a time and in sequence. In the calculator 50 of the instant example, there are 8 digit positions on the display 54 whereby there is a sequence of 8 digits generated by the circuit 52 in rapid succession, beginning with the first column or units digit and concluding with the eighth column or eighth digit of the sequence. A complete cycle in which all eight digits are generated, spans a period of 3 milliseconds, at the conclusion of which cycle the scanning process is repeated. Of course, the complete 8 digit number appearing in the display 54 is generated and fully displayed every 3 milliseconds, a time span so short that the human eye recognizes the number displayed as constant and continuous, rather than pulsating in a sequential and intermittant manner. Time division multiplexing of this type greatly reduces the amount of circuitry and connecting wiring required between the calculator logic circuitry 52 and the display 54 and is popular with calculator manufacturers for that reason.

The 7-segment to decimal decoder 56 and the digit selection logic circuit 68 of the instant invention is adapted to take advantage of this multiplexing principal. The logic circuit 68 makes use of the timing or clock pulses, designated D1–D8 in FIG. 6 as generated in the calculator logic circuit 52. The timing pulses D1–D8 are conveyed via a series of 8 timing lines 70 to the circuit 68 where they each drive one terminal of a different 2-input NAND gate 72. It should be remembered here that the timing pulse D8, for example, occurs during a particular 3 microsecond interval when a digit is electronically registered in only the eight digits position or column of the display 54. During this brief time interval, no other digits positions of the display 54 are energized with a 7-segment coded digit signal.

Assume that now a blind person touches with his fingertip the 1 terminal 62 located in the eighth column of the matrix (extreme upper left terminal of the matrix 60 of FIG. 5a). Since all of the 1's terminals 62 are interconnected, each of the 1's terminals along the top row of the matrix 60 are energized along the 1 line of the lines 58. However, as the user shorts the 1 terminal 62 in the eighth column of the matrix 60 to the substrate 66, a signal C8 appears along the matrix output line 64 of column 8. At this time none of the remaining lines 64 carry a signal thereon.

The signal C8 then appearing on the line 64 from column 8 appears at the C8 input terminal of the circuit 68 (FIG. 6) after which it is inverted by an inverter 74 and fed to a NAND gate 72 in its' path as shown. Since a digit is being displayed in column 8 of the display 54 under this example, the timing pulse D8 will occur every 3 milliseconds at the D8 terminal of the subject NAND gate 72 exactly at the same times as the pulses C8 appear at the other input terminal of the same gate. Accordingly, the subject gate 72 will conduct along an output line 76 and will energize a 4 input NOR gate 78 in its' path. In turn, the subject NOR gate 78 will conduct through line 80 to an inverter 82 and from thence will energize an output NOR gate 84 to produce a pulse signal along an output line 86, designated DS. The signal DS of the present example is indicative that the user of the matrix has touched an energized 1 on the matrix 60 in the column that corresponds to the column in which a 1 is present in the display 54 (column 8). The user recognizes that he is then touching a 1 in column 8 of the matrix 60 by touch.

Figure 7:
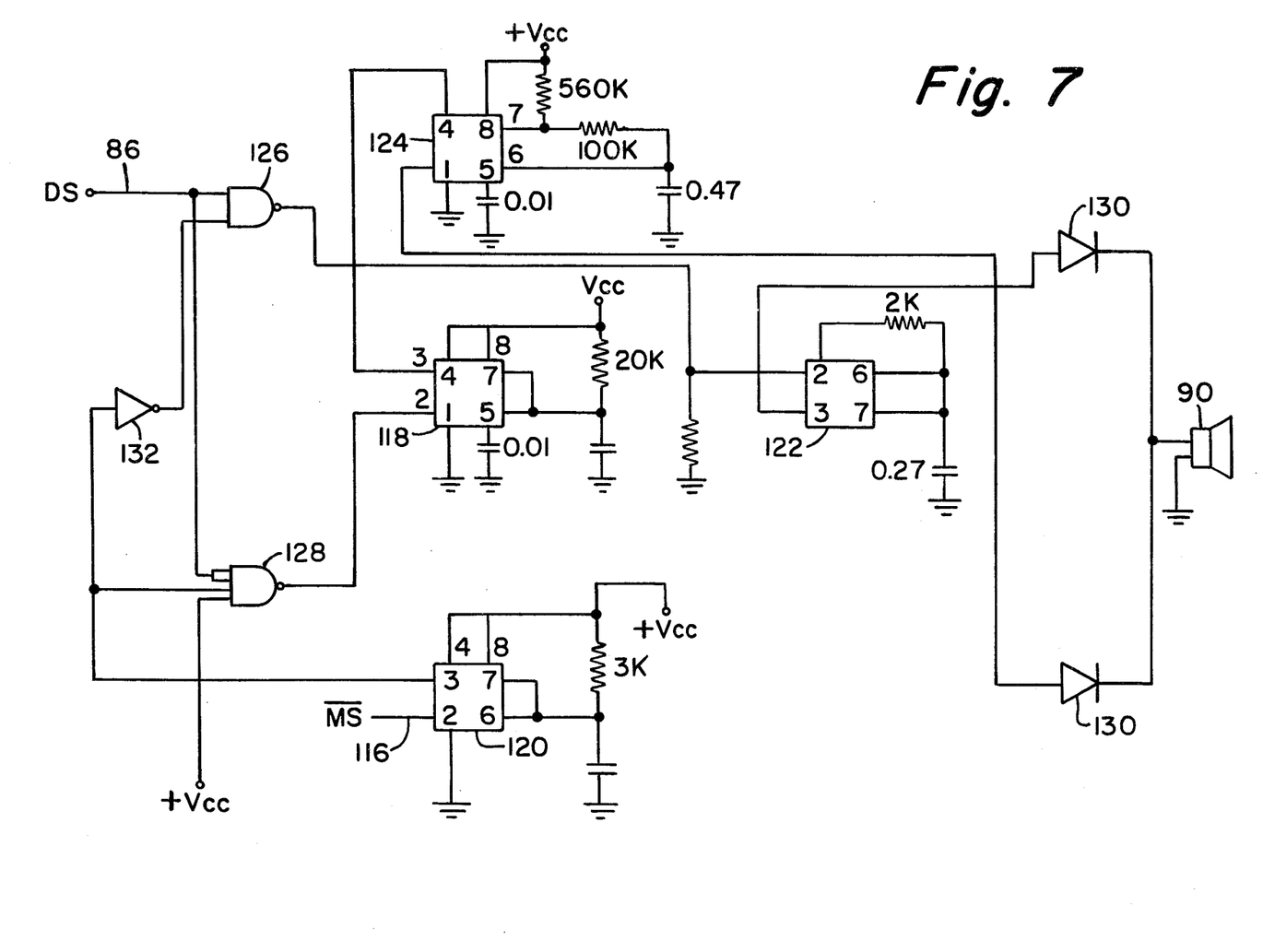
FIG. 7 shows one example of audio transducer logic circuitry which may be used in the logic circuit of FIG. 4.

In turn, the signal DS thus produced follows the line 86 to an audio transducer logic circuit 88, an example of which is shown in FIG. 7. The circuit 88, in turn, drives a speaker 90 of any suitable type to produce a steady audio tone recognizable to the user of the matrix 60. Thus, by touch, the user recognizes a 1 in column 8 of the matrix 60. If at the same time, he hears an audio tone from the speaker 90, he then recognizes that the 1 in column 8 of the matrix 60 is the same digit as is on the visual display in column 8 of the calculator display 54.

Now suppose, by way of example, that the user touches the 1's digit in column 7 of the matrix 60 and assume further that, at that time, a different digit appears in column 7 of the display 54. Since all of the 1 terminals 62 of the matrix 60 are interconnected, when the user touches the 1 terminal in column 7 thus shorting it to the substrate 66, a signal C7 will occur on that particular line 64, which will be fed to the digit selection logic circuit 68. However, the C7 pulse signal occurring at the NAND gate 72 in its' path in the circuit 68 of FIG. 6, will not occur during the same time intervals as the timing pulse D7 appearing at the other input terminal of the same gate. Consequently, the subject gate will not conduct, no output signal DS will occur on output line 86, and no audio tone will be generated by the audio transducer logic circuit 88 and the speaker 90. Thus, the user realizes that a 1 does not appear in the seventh column of the visual display 54 and he may thus move his finger down the seventh column of the matrix 60 until he does engage a set of braille coded terminals which produces a sonic signal in the same manner as previously described with respect to the 1 in column 8.

Referring now only to the 7-segment to decimal decoder circuit of FIG. 5, a specific example of components shown therein will now be provided. The circuit utilizes a calculator chip 92 which may be a Caltex type CT5005; a series of five transistors 94; each of which may be type 2N3638; three inverters 96, type 7404; and four 2 input NAND gates 98, type 7400. A series of resistors 100 each bar the ohmic resistance value as shown. The signals employed to drive the circuit, designated SA, SB, SE, SF and SG are derived from the same source as the signals of the calculator 50 which drive the bars designated a, b, e, f and g, respectively, of a digit register 102 of the display 54. Signals SC and SD used to drive the bars c and d of the digit register 102 are redundant and are, therefore, not utilized by the converter circuit of the instant example.

Also shown in FIG. 5 is a circuit 104 consisting of a 3 kiloohm resistor 106 and an inverter 108 adapted to sample a decimal point signal SP used to drive the decimal point p of the digit register 102. The decimal point signal SP is supplied directly from the circuit 104 to a series of decimal point terminals 110 located along the bottom row of the matrix 60 between adjacent columns of braille coded terminals 62. The decimal point circuit 104 is most conveniently shown in FIG. 5 along with the decoder circuitry but forms no part of the latter, since the decoder 56 does not operate on the decimal point signal SP in any way.

Referring now to FIG. 6, the digit selection logic circuit 68 of the present example may be obtained as follows. There are a series of 8 resistors 112 which may each be 11 megohms in value. The 10 inverters 74 and 82 may be obtained using 2 HEX inverter integrated microcircuit chips, RCA type CD4009AD. Each such HEX inverter chip contains 6 inverters, only 10 of which will be used in this circuit. However, the remaining 2 unused inverters of the set could be used elsewhere in the system of circuits explained herein, if desired. The NOR gates 78 and 84, 3 in all, may be obtained using RCA type CD4012A microcircuit chips. A pair of 2 input NAND gates 112 and 114 may be obtained from a single chip, RCA type CD4011A or the like.

The NAND gate 112 has one of its' input terminals connected to the source of the negative digit signal SG generated by the calculator 50 when the number displayed in the display 54 carries a minus sign. The minus sign signal SG occurs simultaneously with a clock pulse D11, also generated by the calculator 50 for the purpose of gating the minus sign indicator of the display 54 into an operative state. The clock pulse signal D11 of the calculator 50 is sampled and applied to the other input terminal of the NAND gate 112. When these two signals SG and D11 occur simultaneously at the input terminals of the gate 112, a minus sign signal $\overline{MS}$ is generated on an output line 116 which signal $\overline{MS}$ is, in turn, transmitted to the audio transducer logic circuit 88 as seen in FIG. 7. The circuit of FIG. 7 is adapted to produce a beeping or intermittant audio tone when the minus sign signal $\overline{MS}$ is introduced simultaneously with the digit signal DS, recognizable to the user as indicative of a negative number.

Overflow information, indicative that a number calculated by the circuit 52 is too large to be displayed in the display 54, such as, for example, when division by zero has been attempted, is conveyed by the calculator 50 be means of a signal SF occurring simultaneously with the clock pulse D11. The signal SF generated by the circuit 52 is sampled by the circuit 68 as shown in FIG. 6 and is applied to the 2 input NAND gate 114 along with the timing pulse D11. When an overflow condition occurs in the display 54, the signals SF and D11 appear simultaneously at the input terminals of the gate 114, whereby an overflow signal is applied to the NOR gate 84 thus producing a continuous audio tone in the speaker 90 (FIGS. 4 and 7) until the calculator 50 is cleared of the overflow condition.

Referring now to FIG. 7, a specific example of the audio transducer logic circuit 88 will now be provided. There are 4 timer microcircuits chips 118, 120, 122 and 124 shown which are multivibrator chips. Type NE555 multivibrator chips may be employed for each of these wherein the chips 118, 120 and 122 are connected in the usual and well-known manner to form monostable multivibrators. The remaining chip 124 is connected to form an astable multivibrator. Also shown is a two input NAND gate 126, RCA type CD4011A, and a 4 input NOR gate 128, RCA type CD4012A, and a pair of diodes 130 which may be obtained using type IN918's. The terminal connections marked on the chips 118–124 are those of the particular chips recommended for use in this example. The resistors and capacitors shown bear the values indicated in FIG. 7. An inverter 132 used in the circuit may be obtained from an unused inverter on one of the inverter chips used in the other circuits of the invention, namely RCA type CD4009AD. The value of the voltages $V_{cc}$ to be applied to the circuit of FIG. 7 as shown is 5 volts. The speaker 90 of FIG. 7 is part of a Mallory sonalert, type SC628H which generates a 4500$H_z$ tone.

Although the instant invention has been described with respect to specific details of certain preferred embodiments thereof, it is not intended that such details limit the scope of the instant invention except insofar as is set forth in the following claims.

I claim:

1. In an improved electronic instrument of the type comprising a digital logic circuit having a decimal digital data source, the improvement of which comprises
    a touch controlled switching matrix comprising
        an electrically conductive substrate,
        at least one series of raised electrically conductive terminals disposed on said substrate and divided into coded groups, each of said groups being representative of a different digit in the decimal system from 0 through 9, and
        means for insulating said terminals from said substrate in such a manner as to permit any selected one of said groups to be shorted with a finger to said substrate, each of said groups being electrically connected to said data source,
    means for generating an audible signal responsively connected to said substrate for generating said signal when one of said groups bearing a signal from said data source is shorted with a finger to said substrate.

2. An electronic circuit adapted for operative association with a digital electronic instrument of the type comprising logic circuitry adapted to generate a timed sequence of digital signals, each of said signals being representative of decimal digit of a multi-digit number and containing components coded in segmented logic, said electronic circuit comprising
    means for sampling a portion of each of said digital signals and for converting each of said portions from said segmented logic into an equivalent decimal coded signal,
    a switching matrix comprising
        an electrically conductive substrate being electrically divided into a plurality of segments, each of said segments being representative of different digit positions of said multi-digit number,
        an array of raised electrical terminals disposed of said substrate and being divided into a plurality of sets, each of said sets representing a different one of said digit positions and containing coded groupings of said terminals representing the digits 0 through 9, each of said sets being disposed on a different one of said segments,
        means for insulating said terminals from said substrate in such a manner as to permit any selected one of said groupings to be shorted by a fingertip to said substrate, each of said groupings representing the same decimal digit being electrically connected to a corresponding digital signal output source of said sampling and converting means,
    digital selection logic means comprising
        a plurality of input terminals, each of said input terminals being responsively connected to a different one of said segments,
        a plurality of timing signal terminals, each of said timing signal terminals being connectible to a source of timing signals in said instrument representative of a different one of said digit positions,
        means for comparing the simultaneous occurrence of said signals of said input and timing signal terminals for generating a signal when one of said groupings is shorted to said substrate which is energized by a signal from said sampling and converting means, said energized grouping being contained in one of said sets representative of one of said digital signals of said ordered sequence, and
    audio transducer logic circuitry adapted to generate an audible sound responsively connected to said comparing means.

* * * * *